(12) United States Patent
Pattee et al.

(10) Patent No.: US 6,640,363 B1
(45) Date of Patent: Nov. 4, 2003

(54) MOBILE IMAGING TABLE PIVOT MECHANISM

(75) Inventors: Jeffrey Wayne Pattee, Salt Lake City, UT (US); Barry Keith Hanover, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 21 days.

(21) Appl. No.: 09/688,518

(22) Filed: Oct. 16, 2000

(51) Int. Cl.⁷ .............................................. A61G 13/00
(52) U.S. Cl. .................... 5/601; 5/607; 5/608
(58) Field of Search .......................... 5/601, 607, 608, 5/611, 600, 609, 610

(56) References Cited

U.S. PATENT DOCUMENTS

| | | |
|---|---|---|
| 3,450,132 A | 6/1969 | Ragon et al. |
| 3,997,926 A | 12/1976 | England |
| 4,101,120 A * | 7/1978 | Seshima .................. 378/209 |
| 4,195,829 A * | 4/1980 | Reser ....................... 5/607 |
| 4,572,493 A * | 2/1986 | Hubert ...................... 5/608 |
| 4,715,591 A | 12/1987 | Dragmen, Sr. |
| 4,761,000 A | 8/1988 | Fisher et al. |
| 4,769,584 A | 9/1988 | Irigoyen et al. |
| 5,018,712 A * | 5/1991 | Schaefer ................... 5/607 |
| 5,131,105 A | 7/1992 | Harrawood et al. |
| 5,205,004 A | 4/1993 | Hayes et al. |
| 5,528,782 A * | 6/1996 | Pfeuffer et al. |
| 5,583,901 A | 12/1996 | Reitter et al. |
| 5,621,933 A * | 4/1997 | Knapp et al. |
| 5,657,498 A | 8/1997 | Hum |
| 5,771,511 A * | 6/1998 | Kummer et al. ............. 5/600 |
| 6,038,718 A | 3/2000 | Pennington et al. |
| 6,070,281 A | 6/2000 | Reich |
| 6,269,499 B1 | 8/2001 | Amir |
| 6,353,949 B1 | 3/2002 | Falbo |

FOREIGN PATENT DOCUMENTS

DE        2 260 140        12/1972

* cited by examiner

*Primary Examiner*—Heather Shackelford
*Assistant Examiner*—Fredrick Conley
(74) *Attorney, Agent, or Firm*—McAndrews, Held & Malloy, Ltd.; Peter J. Vogel; Michael A. Dellapenna

(57) ABSTRACT

A patient table with a table pivot member is disclosed. A patient support surface supporting a patient during a medical procedure is supported by a base which includes telescopic members to move the patient support surface vertically. A table pivot member connects the patient support surface to the base. The table pivot member enables the patient support surface to pivot in at least one of tilt and lateral roll directions with respect to the base. An actuating element composed of at least two actuators is connected between the patient support surface and the base to drive the patient support surface in at least one of tilt or lateral roll directions.

21 Claims, 5 Drawing Sheets

MOBILE IMAGING TABLE PIVOT MECHANISM

CROSS-REFERENCE TO RELATED APPLICATIONS

Not applicable.

STATEMENT REGARDING FEDERALLY SPONSORED RESEARCH OR DEVELOPMENT

Not Applicable.

BACKGROUND OF THE INVENTION

The preferred embodiments of the present invention generally relate to an apparatus and a method for supporting patients during medical procedures. More particularly, the preferred embodiments of the present invention are directed to a movable medical patient support system with a pivot mechanism that provides for full motion and low table height.

There currently exists a wide range of medical patient support systems for medical applications, each designed to be used for specific medical procedures. However, in all cases, the medical patient support system includes two or three essential components. Usually, a patient table is attached to a supporting mechanism and a means to move the patient table in various directions, including up and down and/or side to side. The moving mechanism may be manually operated or may be power assisted. Because stopping a procedure to reposition a patient can be time-consuming and sometimes even dangerous, the ability to position patients quickly and accurately during medical procedures is important to clinicians.

Conventional medical patient support systems typically provide two degrees of freedom corresponding to 1) lateral roll and 2) tilt. The latter movement is also referred to trendelenburg motion. Although conventional medical patient support systems provide for full motion of the patient table, they do so at the expense of table design efficiency. The design inefficiency arises because conventional medical patient support systems are commonly comprised of one actuator that allows the table to tilt up and down and a separate actuator that allows the table to roll laterally. The joint which provides tilt capability includes a shaft on a bearing mechanism. The patient table rotates on this shaft in the tilt direction. However, the entire assembly supporting the bearing is situated on another shaft that supports rotation only in the lateral roll direction. Because these shafts, or pivot points, are stacked, the retracted height of conventional medical patient support systems is necessarily taller than it to would be in the absence of such stacking. And because the entire structure is rotated, requiring one of the actuators to roll and/or tilt with the other one, more physical space is consumed by this motion, resulting in an inefficient design that operates in a cumbersome manner.

A need, therefore, exists for an improved medical patient support system that provides a patient table permitting full motion of the patient table while providing a lower table height than currently exists in conventional medical patient support systems.

BRIEF SUMMARY OF THE INVENTION

A preferred embodiment of the present invention includes a medical patient support system comprising a patient table with a table pivot member. A patient support surface supporting a patient during a medical procedure is supported by a base which includes telescopic members to move the patient support surface vertically. A table pivot member connects the underside of the patient support surface, known as the pivot plate, to the base. The table pivot member enables the patient support surface to pivot in at least one of tilt and lateral roll directions with respect to the base. An actuating element comprised of at least two actuators is connected between the pivot plate and the base to drive the patient support surface in at least one of tilt or lateral roll directions.

One aspect of a preferred embodiment of the present invention is the use of at least two actuators to achieve the desired movement of the patient support surface. The actuators are arranged in a cross-shaft configuration, and work together to move the patient support surface in both tilt and lateral roll directions. Because the preferred embodiment of the claimed invention uses a cross-shaft, rather than a stacked, configuration, the effective retracted height of the patient table is shorter than that of conventional patient tables which employ stacked shafts.

Another aspect of a preferred embodiment of the present invention is the use of two actuators resulting in a smaller footprint and a more compact design.

BRIEF DESCRIPTION OF THE SEVERAL DRAWINGS

DETAILED DESCRIPTION OF THE INVENTION

Figure 1:
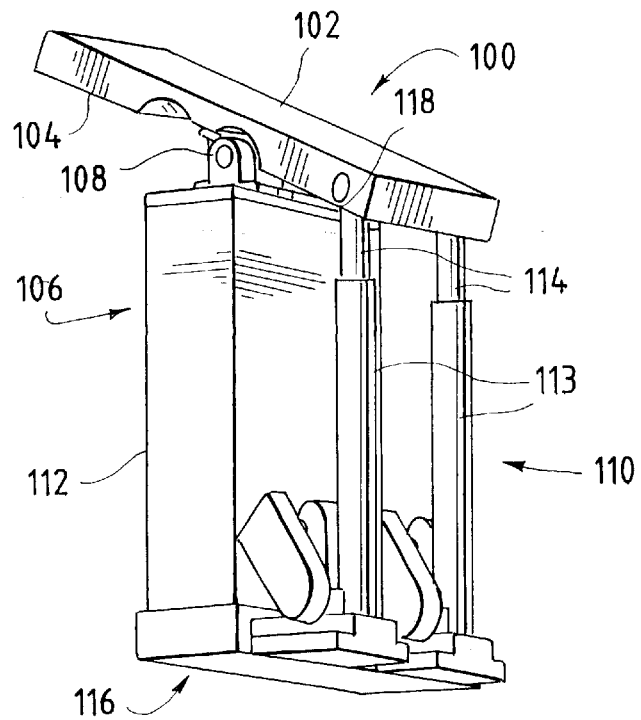
FIG. 1 illustrates a patient table employing a table pivot member, with patient support surface in a tilted forward orientation in accordance with a preferred embodiment of the present invention.
Figure 2:
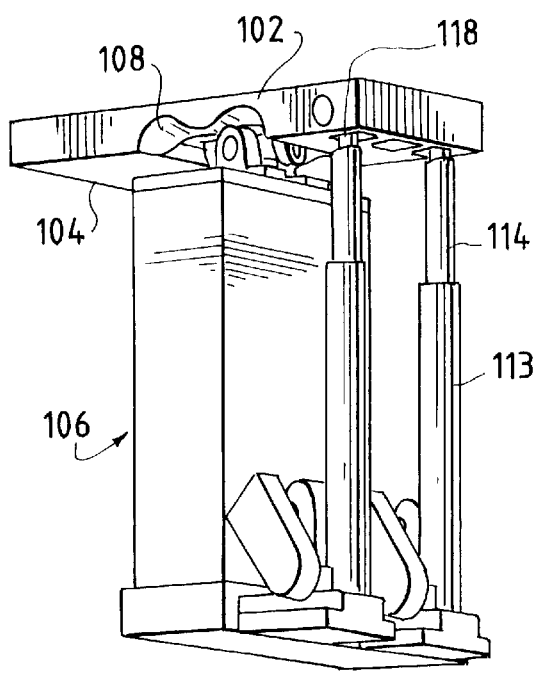
FIG. 2 illustrates a patient table employing a table pivot member, with patient support surface in a level orientation in accordance with a preferred embodiment of the present invention.
Figure 3:
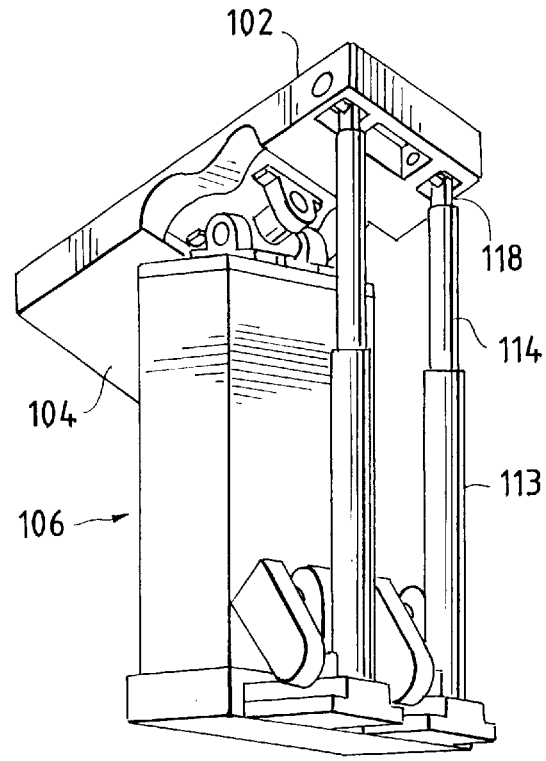
FIG. 3 illustrates a patient table employing a table pivot member, with patient support surface in a tilted back and left orientation in accordance with a preferred embodiment of the present invention.

FIGS. 1, 2, and 3 show a patient table employing a table pivot member, with the patient support surface 102 oriented in different positions. FIG. 1 illustrates a patient table 100 with patient support surface 102 in a tilted forward orientation in accordance with a preferred embodiment of the present invention. Referring to FIG. 1, the patient table 100 includes a patient support surface 102, a pivot plate 104, a base 106, a table pivot member 108 pivotally connecting the pivot plate 104 to the base 106, and an actuating element 110 connected between the pivot plate 104 and the actuator support plate 116.

The pivot plate 104 is mounted on the underside of the patient support surface 102 and is pivotally connected to the base 106 by the table pivot member 108. The table pivot member 108 is mounted horizontally on the top surface of the base 106. The base 106 is further comprised of lift columns 112.

The actuating element 110 is comprised of actuators 113, telescopic members 114, and actuator pivot members 118. The telescopic members 114 reside in the inner shell of the actuators 113, and move the patient support surface 102 in a vertical direction. The actuator pivot members 118 pivotally connect the pivot plate 104 and the telescopic members 114. The actuating element 110 rests on an actuator support plate 116.

The table pivot member 108 moves to effect the tilted orientation of the patient support surface 102 as shown in FIG. 1. The movement of the table pivot member 108 may be in response to a contemporaneous request from a user. Alternatively, the movement of the table pivot member 108 may be automatic in response to predetermined table coordinate values set by a user. In any case, the table pivot member moves in the tilt direction, tilting forward the pivot plate 104 and, in turn, the patient support surface 102.

FIG. 2 illustrates a patient table 100 employing a table pivot member 108, with patient support surface 102 in a level orientation in accordance with a preferred embodiment of the present invention. In the level orientation, the table pivot member 108 is neither tilting nor rolling laterally. Hence, the patient support surface 102 remains in a horizontal position, aligned in parallel with the table pivot member 108. FIG. 3 illustrates a patient table 100 employing a table pivot member 108 with patient support surface 102 in a tilted back and left orientation in accordance with a preferred embodiment of the present invention. Here, the table pivot member 108 moves in both the tilt and lateral roll directions, tilting back and left the pivot plate 104 and, in turn, the patient support surface 102. The telescopic members 114 are extended as well to position the patient support surface 102 to the required height.

Figure 4:
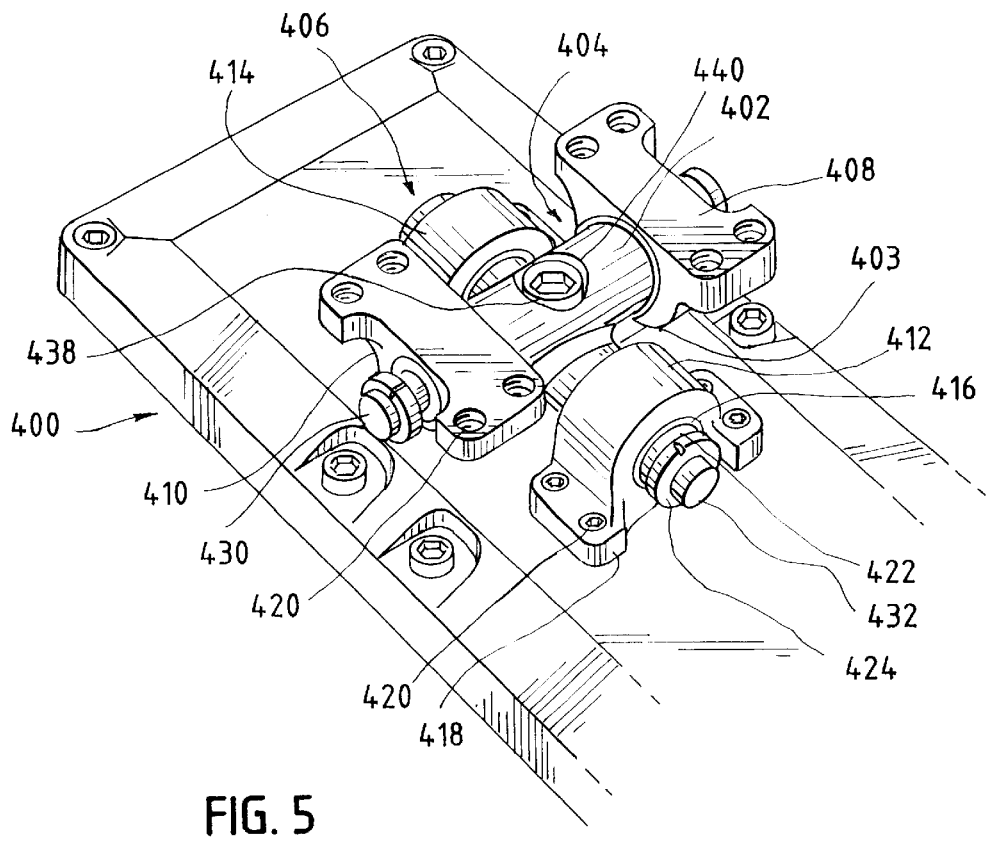
FIG. 4 illustrates an overhead view of a table pivot member for permitting tilt and lateral roll in accordance with a preferred embodiment of the present invention.
Figure 5:
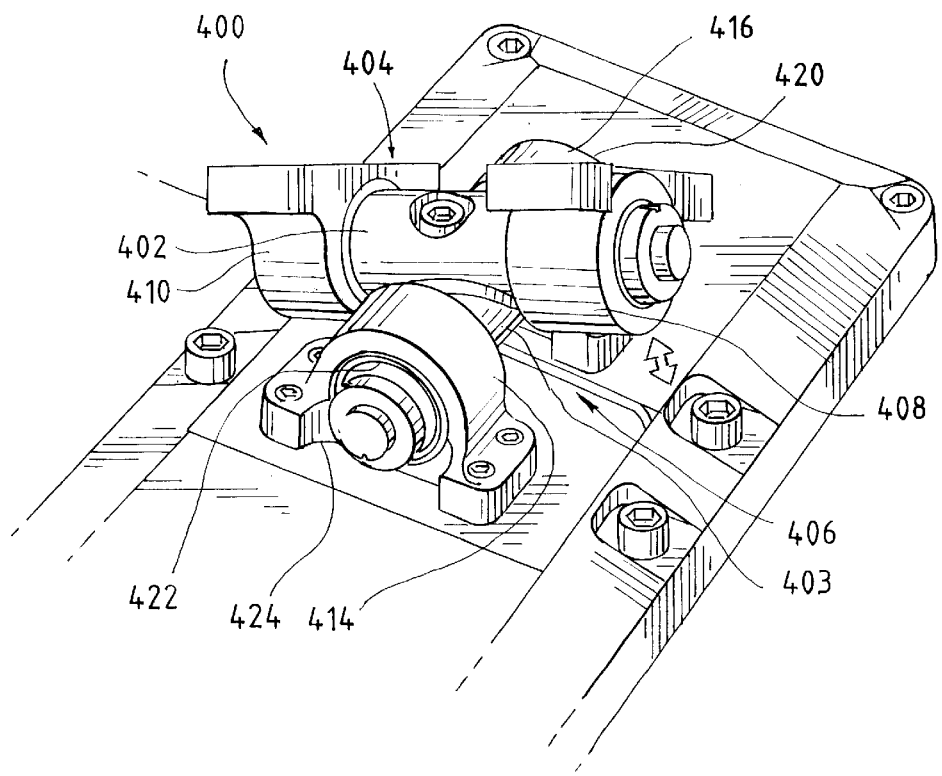
FIG. 5 illustrates a side view of a table pivot member for permitting tilt and lateral roll in accordance with a preferred embodiment of the present invention.

FIGS. 4 and 5 illustrate overhead and side views, respectively, of the table pivot member 108 for permitting tilt and lateral roll of the patient support surface 102 in accordance with a preferred embodiment of the present invention. FIG. 4 shows an overhead view of a table pivot member 108 with two shafts 402 and 403 aligned perpendicularly to one another and having axes of rotation offset vertically with respect to one another.

In one embodiment, the table pivot member 108 includes a gimbal member 400 with a perpendicular shaft configuration. The gimbal member 400 includes upper and lower shaft assemblies 404 and 406 securely formed with one another. Optionally, the upper and lower shaft assemblies 404 and 406 may be bolted to one another, welded together, injection molded as a unitary structure, cast as a unitary structure, and the like. The upper shaft assembly 404 includes pillow blocks 408 and 410 formed on opposite ends thereof, while the lower shaft assembly 406 includes pillow blocks 412 and 414 formed on opposite ends thereof. The upper shaft assembly 404 and associated pillow blocks 408 and 410 are formed along a longitudinal axis extending parallel to the length of the patient support surface 102. The lower shaft assembly 406 and associated pillow blocks 412 and 414 are formed to extend along a longitudinal axis extending in a direction perpendicular to the length of the patient support surface 102. The longitudinal axes of the upper and lower shaft assemblies 404 and 406 are perpendicular to one another and offset vertically from one another slightly by a distance substantially corresponding to a diameter of the upper or lower shaft assemblies 404 and 406.

The pillow blocks 408–414 include semicircular bearing races 416 integrally formed with outer base flanges 418. The base flanges 418 have flat lower surfaces configured to securely engage the corresponding surface on the patient support surface 102 and/or base 106. The base flanges 418 include threaded openings 420 therethrough to receive bolts that secure the pillow blocks 408–414 to the corresponding one of the pivot plate 104 and base 106. The bearing races 416 receive bearings 422 rotatably mounted therein. The bearings 422, in turn, rotatably receive one of shafts 402 and 403. The upper and lower shaft assemblies 404 and 406, pillow blocks 408–414, and bearings 422 cooperate to retain the shafts 402 and 403 in a desired perpendicular orientation with respect to one another, while locating the shafts 402 and 403 vertically close to one another. For instance, the central rotational axes of shafts 402 and 403 may be located vertically from one another by a distance substantially equal to the outer diameter of one of the upper and lower shaft assemblies 404 and 406.

Outer ends of the upper shaft assembly 404 include upper outer shaft sections 430 formed integrally therewith. The upper outer shaft sections 430 are received within bearings 422 in the pillow blocks 408 and 410. The bearings 422 are held in place by a nut 424. The lower shaft assembly 406 similarly includes lower outer shaft sections 432 formed integrally therewith and extending in opposite directions along a longitudinal axis of the lower shaft assembly 406. The lower outer shaft sections 432 are rotatably received within bearings 422 in the pillow blocks 412 and 414.

The upper and lower shaft assemblies 404 and 406 include a threaded recess 438 extending therethrough in a vertical direction substantially orthogonal to the longitudinal axes of the upper and lower shaft assemblies 404 and 406. The threaded recess 438 receives a bolt 440 to afford added strength to the gimbal member 400.

The gimbal member 400 is formed with a low vertical profile such that the flanges 418 of pillow blocks 408 and 410 are formed within a horizontal envelope that overlaps the envelope of the flanges 418 on the pillow blocks 412 and 414. Optionally, the longitudinal axes of the upper and lower shaft assemblies 404 and 406 may be in a common plane, such that the pillow blocks 408–414 all lie within a common horizontal envelope to reduce the vertical profile of the gimbal member 400.

The gimbal member 400 is formed within a horizontal envelope having upper and lower planar surfaces substantially corresponding to the bottom surface of the pivot plate 104 and the upper surface of the base 106 to which the gimbal member 400 is mounted.

Pillow blocks 408 and 410 are secured to the pivot plate 104 by bolts received through the threaded openings 420. Similarly, pillow blocks 412 and 414 are secured to the lift columns 112 in the base 106 by bolts received through the threaded openings 420. Pillow blocks 408 and 410 mounted on the pivot plate 104 allow the patient support surface 102 to roll laterally, while pillow blocks 412 and 414 mounted to the lift column 112 allow the patient support surface 102 to tilt. Thus, the combined tilting and rolling motion is effected on a spherical path.

The gimbal member 400 illustrated in FIG. 4 is neither tilting nor rolling laterally. Hence, the patient support surface 102 remains in a horizontal, or level, orientation as shown in FIG. 2, with the patient support surface 102 aligned in parallel with the table pivot member 108. In contrast, FIG. 5 illustrates, in accordance with a preferred embodiment of the present invention, a gimbal member 400 tilting and laterally rolling to place a patient support surface 102 in a specified position. The upper and lower shaft assemblies 404 and 406, pillow blocks 408–414, and bearings 422 retain the shafts 402 and 403 in a perpendicular orientation with respect to one another, while effecting the desired tilt and/or lateral roll of the patient support surface 102. The pillow blocks 408 and 410 are secured to the pivot plate 104 by bolts received through the threaded openings 420. Consequently, as the pillow blocks 408 and 410 rotate, the pivot plate 104 moves in the same corresponding direction.

Figure 6:
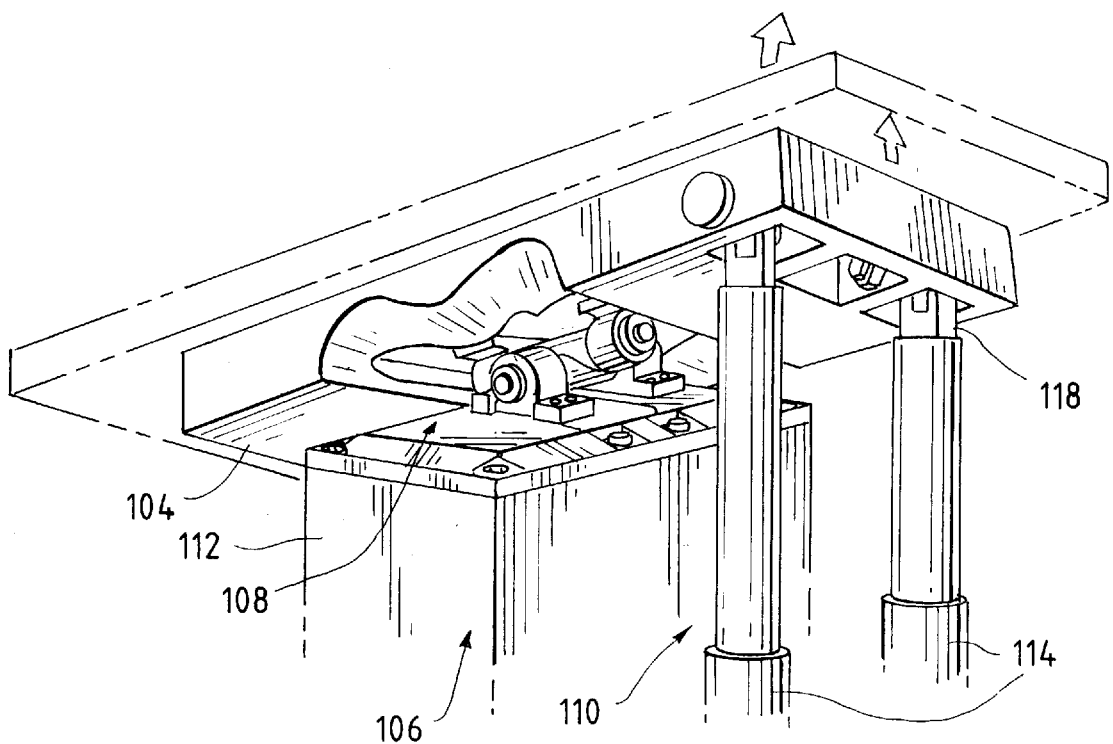
FIG. 6 illustrates the table pivot member pivotally connecting the pivot plate to the base in accordance with a preferred embodiment of the present invention.

FIG. 6 illustrates a detailed view of the table pivot member 108 pivotally connecting the pivot plate 104 to the base 106 in accordance with a preferred embodiment of the present invention. FIG. 6 also illustrates the actuator pivot members 118 which provide a connection between the pivot plate 104 and the telescopic members 114. Referring to FIG. 6, the table pivot member 108 mounted to the lift columns 112 of the base 104 is shown effecting a simultaneous tilt and lateral roll of the pivot plate 104. As a result, the patient support surface 102 moves in a corresponding motion. The actuating element 110, comprising actuators 113, telescoping members 114, and actuator pivot members 118, provides for appropriate positioning of the patient support surface 102 with respect to height.

Figure 7:
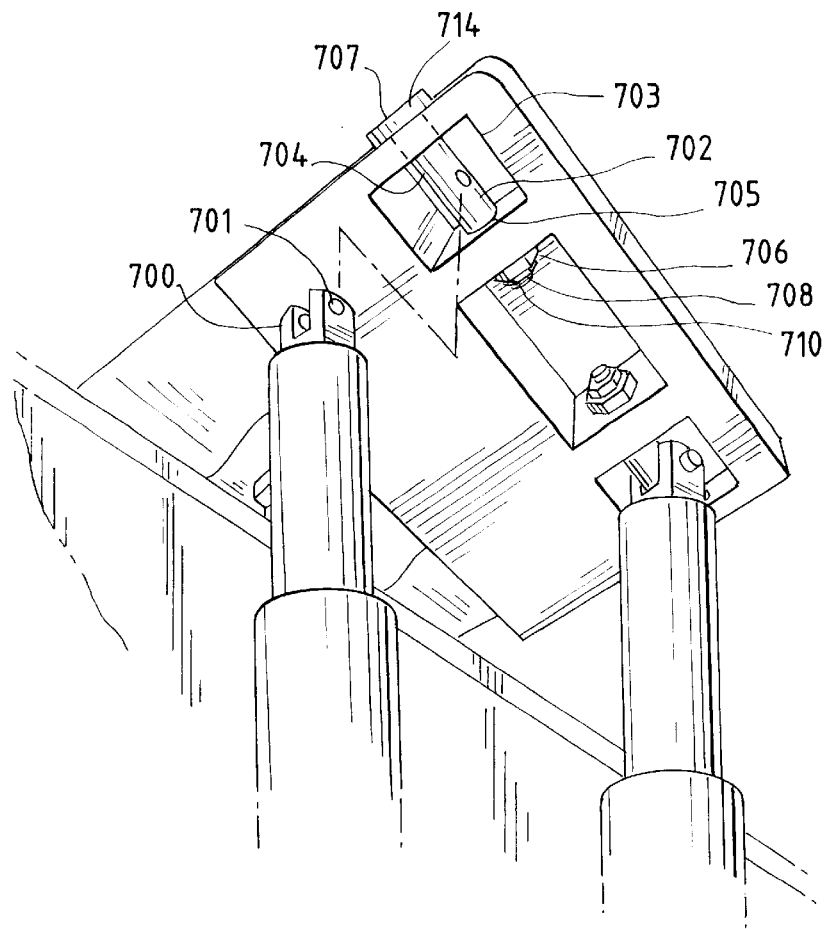
FIG. 7 illustrates telescopic members connecting to a pivot plate by actuator pivot members in accordance with a preferred embodiment of the present invention.

FIG. 7 illustrates another view of the telescopic members 114 connecting to a pivot plate 104 in accordance with a preferred embodiment of the present invention. The telescopic members 114 rest within the actuators 113 and are connected to the pivot plate 104 by the actuator pivot member 118. The actuator pivot member 118 is comprised of a U-joint 700 residing within the upper portion of the telescopic member 114. The U-joint 700 includes a U-joint opening 701 on each of the vertical sides of the U-joint 700. The actuator pivot member 118 is further comprised of a notched shaft 702. The notched shaft 702 contains a shaft opening 704 at its center for receiving a bolt, the bolt securing the U-joint 700 at the U-joint opening 701 to the notched shaft 702 at the shaft opening 704. The notched shaft 702 rests within one of a multiple of table recesses 703 carved out of the pivot plate 104. Each table recess 703 contains two table recess openings 705 and 707 located on opposite sides of one another to allow the notched shaft 702 to be inserted longitudinally, with the shaft opening 704 positioned downward to align and interlock with the U-joint opening 701. Though the notched shaft 702 is positioned in the open portion of the U-joint 700 and fastened to the U-joint 700 by a bolt, the notched shaft 702 may pivot within the U-joint 700 in a lateral direction.

Figure 8:
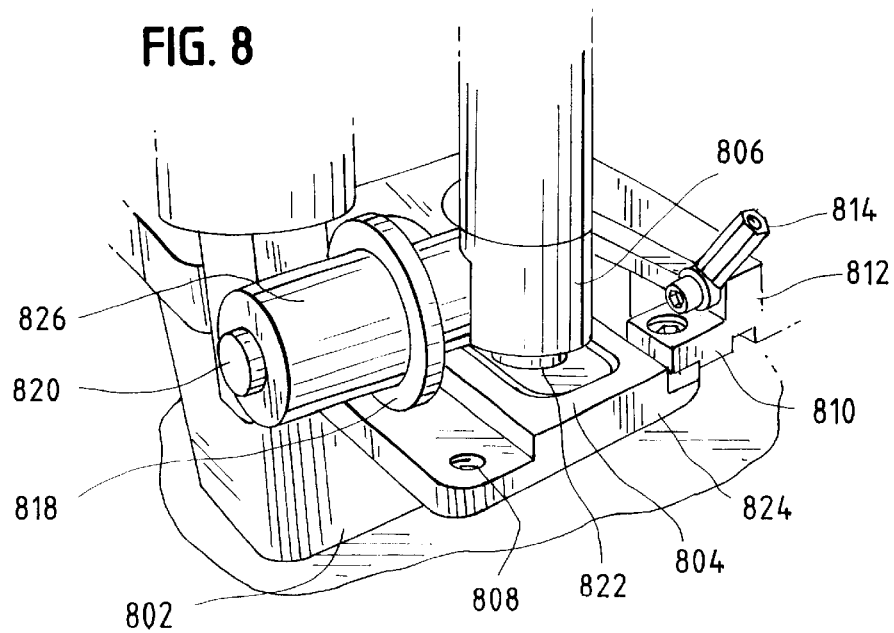
FIG. 8 illustrates an actuating element resting on an actuator support plate in accordance with a preferred embodiment of the present invention.

The notched shaft 702 is secured in the table recess 703 by a series of bolts and caps. On the end of the notched shaft 702 farthest from the edge of the pivot plate 104, the notched shaft 702 is secured in the table recess 703 by an outer bolt 706, an inner nestled bolt 708, and an open-ended outer cap 710. On the end of the notched shaft 702 closest to the edge of the pivot plate 104, the notched shaft 702 is secured in the table recess 703 by a securing bolt 714 protruding slightly from the edge of the pivot plate 104. FIG. 8 illustrates the actuating element 110 resting on an actuator support plate 116 in accordance with a preferred embodiment of the present invention. The actuator support plate 116 protrudes from and is supported by an actuator support base 802. The actuator support plate 116 includes a support plate recess 804 to receive and affix the lower portion 806 of the actuator 13 to the actuator support plate 116. The actuator support plate 116 also includes actuator support plate openings 808. The actuating support plate openings 808 are used for multiple connection purposes. For example, an actuator support plate opening 808 receives a connection bolt 810 to secure an actuator connecting block 812. The actuator connecting block 812 connects multiple actuator support plates 116, each housing a single actuator 113. Actuating levers 814 coordinate the movement between the actuator support plates 116.

An integral actuator cylindrical shaft 816 extends perpendicularly from the lower portion 806 of the actuator 113 and is encircled by multiple supporting brackets 818. A circular shaft end 820 caps the actuator cylindrical shaft 816. An actuator block base 822 with cylindrical extensions 824 extending from each of the sides of the actuator block base 822 is mounted to the bottom of the lower portion 806 of the actuator 113. The actuator block base 822 rests within the support plate recess 804, and is secured therein by the insertion of at least one of the cylindrical extensions 824 into an actuator support plate opening 808 in the actuator support plate 116.

Figure 9:
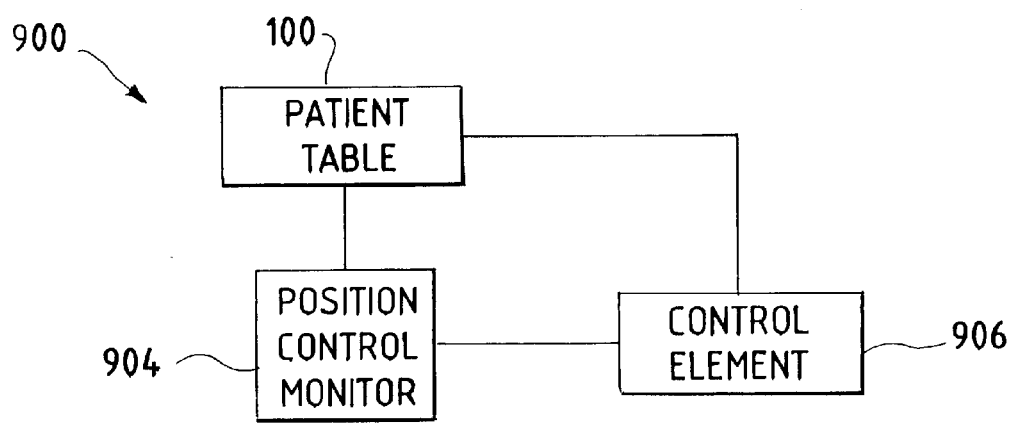
FIG. 9 illustrates a block diagram of a medical patient support system comprising a patient table with a table pivot member in accordance with a preferred embodiment of the present invention.

FIG. 9 shows a block diagram of a medical patient support system 900 in accordance with a preferred embodiment of the present invention. The medical patient support system 900 includes a patient table 100 with a table pivot member 108. A medical patient support system 900 may be used, for example, in performing "triple A" stent procedures in lieu of bypass surgery. Other applications include minimally invasive fluoroscopic imaging procedures, including vascular, endovascular, cardiovascular, coronary, and angiography, selective angiography, and general surgical procedures.

The medical patient support system 900 includes a patient table 100, a position control monitor 904, and a control element 906. Optionally, a medical patient support system 900 may include a user interface. The patient table 100 is comprised of a patient support surface 102, a pivot plate 104, and a base 106. The patient table 100 is further comprised of a table pivot member 108 pivotally connecting the pivot plate 104 to the base 106, and allowing the patient support surface 102 to be moved in at least one of tilt and lateral roll directions. An actuator pivot member 118 pivotally connects the telescopic members 114 to the pivot plate 104.

The patient table 100 is connected to a position control monitor 904 for detecting the location of the patient table 100. The table location may be identified in terms of its tilt and lateral roll coordinates at any given time. The position control monitor 904 may monitor table location through the use of electro-mechanical or optical sensors, or by monitoring servomotor positions to rotation and the like. A control element 906 is connected between the position control monitor 904 and the patient table 100. The control element 906 controls the movement of the patient table 100. The table movement may be effected upon request from an optional user interface or automatically in accordance with a predetermined set of coordinates. The optional user interface may include a personal computer, a hand-held device capable of receiving coordinate data and transmitting such data to the control element 906, or any other mechanism by which specific patient table 100 coordinates may be input and transmitted.

Figure 10:
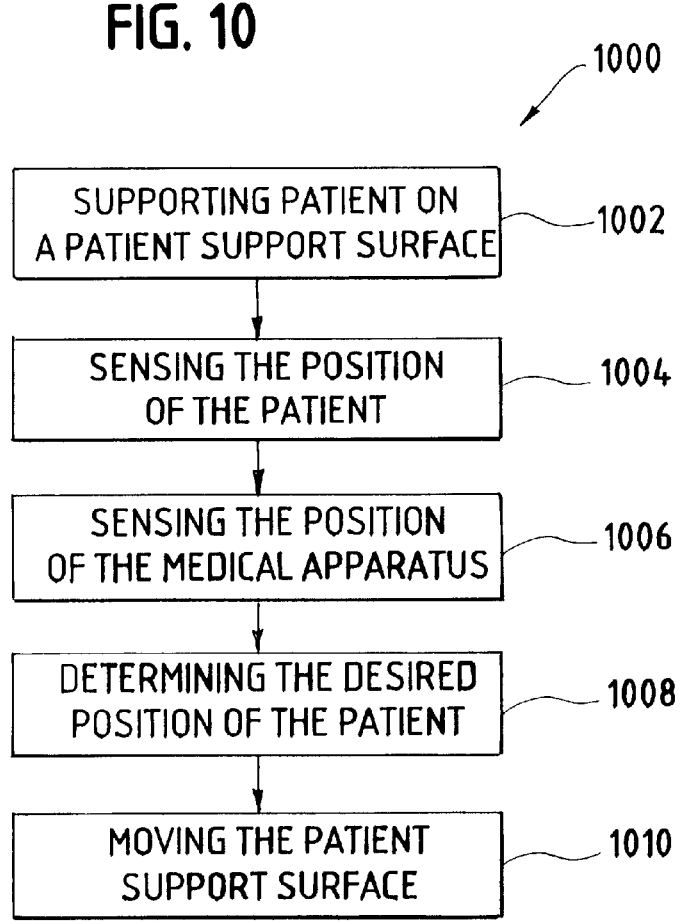
FIG. 10 illustrates a flow diagram of the alignment process in which a patient table with a table pivot mechanism is positioned in relation to a medical apparatus in accordance with a preferred embodiment of the present invention.

FIG. 10 illustrates a flow diagram 1000 of the alignment process in which a patient table with a table pivot mechanism is positioned in relation to a medical apparatus in accordance with a preferred embodiment of the present invention. Such an alignment procedure is used where, for example, a technician performs any number of medical procedures on a patient. For instance, during an x-ray examination employing an arc-shaped component support for an x-ray tube, known as a "C-arm," a patient is arranged between the x-ray tube and the x-ray image intensifier by way of a patient table which is moveable in order to obtain an appropriate orientation and position of the patient relative to the x-ray tube and the x-ray image intensifier.

Referring to FIG. 10, a patient is supported on a patient support surface 102 at step 1002. Next, the position of the patient on the patient support surface 102 is determined with respect to the location of the medical apparatus which is being employed during the particular medical procedure at step 1004. At step 1006, the position of the medical apparatus to be used in the particular medical procedure is determined. Then, at step 1008 the determined position of the patient on the patient support surface 102 is compared to the determined position of the medical apparatus in order to assess the desired location of the patient support surface 102 with respect to the medical apparatus. Finally, at the positioning step 1010, the patient support surface 102 is aligned with the medical apparatus in accordance with the desired position determined in step 1008.

While particular embodiments of the invention have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and the scope of the invention.

What is claimed is:

1. A patient table comprising:
   a patient support surface supporting a patient during a medical procedure;
   a base mounted to said patient support surface said base including telescopic remembers to move said patient support surface;
   a table pivot member pivotally connecting said base to said patient support surface, said table pivot member enabling said patient support surface to pivot in at least one of tilt and lateral roll directions with respect to said base, said table pivot member having a low vertical profile and comprising pivot shafts being located perpendicular to one another, each said pivot shaft having a diameter and being offset vertically from one another by a distance corresponding to one of said diameters;
   a table monitor detecting a position of said patient support surface; and
   an actuating element between said patient support surface and said base, said actuating element driving said patient support surface in said at least one of tilt and lateral roll directions, said table monitor detecting movement of said patient support surface in said at least one of tilt and lateral roll directions.

2. The patient table of claim 1 wherein said base further comprises a lift columns.

3. The patient table of claim 2, wherein said lift columns move said patient table in a vertical direction.

4. The patient table of claim 1 wherein said pivot shafts being inserted into pillow blocks, said pillow blocks mounted on top of said base.

5. The patient table of claim 1, wherein said actuating element is comprised of at least two actuators.

6. The patient table of claim 1, wherein said actuating element is comprised of at least two actuators, said at least two actuators functioning simultaneously to tilt said patient table.

7. The patient table of claim 1, wherein said actuating element is comprised of at least two actuators, said at least two actuators functioning simultaneously to laterally roll said patient table.

8. The patient table of claim 1, said table pivot member further comprising:
   a first said pivot shaft being inserted into a first set of pillow blocks mounted on top of said base; and
   a second said pivot shaft being inserted into a second set of pillow blocks mounted to said patient support surface, said first and second pivot blocks lying within a common horizontal envelope to reduce a vertical profile of said table pivot member.

9. A medical patient support system comprising:
   a patient table comprising:
      a patient support surface support a patient during a medical procedure;
      a base mounted to, and supporting, said patient support surface through a pivot plate, said base including telescopic members to move said patient support surface vertically;
      a table pivot member pivotally connecting said pivot plate to said base, said table pivot member enabling said patient support surface to pivot in at least one of tilt and lateral roll vertical directions with respect to said base, said table pivot member having a cross member with two pivot shafts positioned perpendicularly to one another, said two pivot shafts having a low vertical profile; and
      an actuating element connected between said pivot plate and said bas, said actuating element driving said patient support surface in said at least one of tilt and lateral roll directions;
   a position control monitor for continuously detecting the position, said at least one of tilt and lateral roll directions, of said patient table at any given time; and
   a control element connected between said position control monitor and said patient table for controlling the movement of said patient table.

10. The medical patient support system of claim 9 wherein said table pivot member further comprises upper and lower shaft assemblies comprising a gimbal member, said upper and lower shaft assemblies being one of securely formed with one another, bolted to one another, welded to one another, injection molded as a unitary structure, and cast as a unitary structure.

11. The medical patient support system of claim 9 wherein said base further comprises lift columns.

12. The medical patient support system of claim 9 wherein said pivot shafts being inserted into pillow blocks, said pillow blocks mounted on top of said base.

13. The medical patient support system of claim 9, wherein said actuating element is comprised of at least two actuators.

14. The medical patient support system of claim 9, wherein said actuating element is comprised of at least two actuators, said at least two actuators functioning simultaneously to tilt said patient table.

15. The medical patient support system of claim 9, wherein said actuating element is comprised of at least two actuators, said at least two actuators functioning simultaneously to laterally roll said patient table.

16. The medical patient support system of claim 11, wherein said lift columns move said patient table in a vertical direction.

17. A method for aligning a patient with a medical apparatus, the method comprising:

supporting a patient on a patient support surface during a medical procedure;

sensing at least one of tilt and lateral roll of said patient support surface with respect to a, location of a medical apparatus, sensing the position of said medical apparatus to be used in the medical procedure;

determining at least one of a desired tilt and lateral roll of said patient support surface with respect to said location of said medical apparatus; and positioning said patient support surface with a gimbal member to said at least one of a desired tilt and lateral roll so as to align said patient support surface with said medical apparatus, said gimbal member having a cross member with two rotation shafts positioned perpendicularly to one another and forming a low vertical profile.

18. The method of claim 17 wherein said positioning step comprises using at least two actuators to position said patient support surface to said desired position so as to align said patient support surface with said medical apparatus.

19. The method of claim 17 wherein said positioning step comprises provision of at least two actuators, said at least two actuators functioning simultaneously to tilt said patient support surface.

20. The method of claim 17 wherein said positioning step comprises provision of at least two actuators, said at least two actuators functioning simultaneously to laterally roll said patient table.

21. A patient table comprising:

a patient support surface supporting a patient during a medical procedure;

a base mounted to said patient support surface, said base including telescopic members to move said patient support surface;

a table pivot member having a low vertical profile, said table pivot member comprising a gimbal member having a cross member with two rotation shafts each having an outside diameter and a center rotational axis, said two rotation shafts being positioned perpendicularly to one another, said center rotational axis being offset vertically from one another by a distance, substantially equal to one of said outside diameters, said table pivot member pivotally connecting said base and enabling said patient support surface to pivot in at least one of tilt and lateral roll directions with respect to said base;

a table monitor detecting a position of said patient support surface; and an actuating element between said patient support surface and said base, said actuating element driving said patient support surface in said at least one of tilt and lateral roll directions, said table monitor detecting movement of said patient support surface in said at least one of tilt and lateral roll directions.

* * * * *